United States Patent
Fujinami et al.

(10) Patent No.: US 6,566,014 B1
(45) Date of Patent: May 20, 2003

(54) IONICALLY CONDUCTING MOLECULE, IONIC CONDUCTOR AND PROCESS FOR PRODUCING THE SAME

(75) Inventors: Tatsuo Fujinami, Hamamatsu (JP); Mary Anne Mehta, Hamamatsu (JP)

(73) Assignees: Toyota Jidosha Kabushiki Kaisha, Toyota (JP); Genesis Research Institute, Inc., Nagoya (JP)

(*) Notice: Subject to any disclaimer, the term of this patent is extended or adjusted under 35 U.S.C. 154(b) by 25 days.

(21) Appl. No.: 09/585,423

(22) Filed: Jun. 2, 2000

(30) Foreign Application Priority Data

Jun. 11, 1999 (JP) .......................... 11-165115
Nov. 12, 1999 (JP) .......................... 11-322785

(51) Int. Cl.[7] .......................... H01M 6/18; H01M 6/22
(52) U.S. Cl. .......................... 429/307
(58) Field of Search .......................... 429/188, 304, 429/307, 321, 323; 558/287; 252/62.2

(56) References Cited

U.S. PATENT DOCUMENTS

| | | | |
|---|---|---|---|
| 3,711,411 A | * | 1/1973 | Sawyer et al. |
| 4,110,426 A | * | 8/1978 | Barnhurst et al. |
| 4,211,679 A | | 7/1980 | Mark et al. |
| 4,450,087 A | | 5/1984 | Askew et al. |
| 4,873,353 A | * | 10/1989 | Niebylski |
| 5,891,592 A | | 4/1999 | Mao et al. |
| 6,210,838 B1 | * | 4/2001 | Fujinami et al. ............ 429/188 |

FOREIGN PATENT DOCUMENTS

| | | |
|---|---|---|
| DE | 29 26 269 A1 | 1/1981 |
| DE | 3321713 A1 | 12/1984 |
| EP | 0856901 | 1/1998 |
| EP | 0 856 901 A1 | 8/1998 |
| EP | 0898319 A1 * | 2/1999 |
| EP | 0 903 798 A1 | 3/1999 |
| JP | 08045794 | 2/1996 |
| JP | 08339827 | 12/1996 |
| JP | 10-223258 | 8/1998 |
| JP | 11-003728 A | 1/1999 |
| JP | 11-054151 A | 2/1999 |
| JP | 11-121033 A | 4/1999 |
| JP | 2001-055441 A | 2/2001 |
| WO | 97/16862 | 5/1997 |

OTHER PUBLICATIONS

Mehta et al. ("The use of boroxine rings for the development of high perforance polymer electrolytes", Electrochimica Acta 45 (2000) pp. 1175–1180).*

Yang et al. ("Blended lithium ion conducting polymer electrolytes based on boroxine polymers", Solid State Ionics 140 (2001) 353–359). no month available.*

Search Report issued Apr. 7, 2001 in corresponding French Application No. 00 07 427.

Patent Abstracts of Japan, vol. 013, No. 158 (C–586), Apr. 17, 1989; JP 63 314269A.

Benrabah et al, "Perfluorosulfonate–Polyether Based Single Ion Conductors," Electrochimica Acta, vol. 40, pp. 2259–2264, (1995) no month.

(List continued on next page.)

*Primary Examiner*—Patrick Ryan
*Assistant Examiner*—Susy Tsang-Foster
(74) *Attorney, Agent, or Firm*—Burns, Doane, Swecker & Mathis, LLP

(57) ABSTRACT

An ionic conductor according to the present invention includes an electrolyte salt for ionic conduction, an ionically conducting molecule including a molecular chain which provides an ion conducting pathway and a boroxine ring bonded to the molecular chain and trapping anions resulting from the electrolyte salt, and a structural member for dispersion and immobilization of the ionically conducting molecule and the electrolyte salt therein. The structural material gives the ionic conductor mechanical strength, the ionically conducting molecule provides an ion conducting pathway, and the electrolyte salt gives it ionic conductivity.

6 Claims, 6 Drawing Sheets

OTHER PUBLICATIONS

O'Connor et al, "The Boric Acid Dehydration of Alcohols," vol. 77, pp. 1578–1581, Mar. 20, 1955.

Lappert, "Cyclic Organic Boron Compounds. Part II.[1] Chemicals Properties of n–Butyl Metaborate," pp. 3256–3259 (1958) no month.

Abel et al., "The Trialkylsilyl Esters of Boron," pp. 690–693 (1959) no month.

Finch et al, "Boron Ring Compounds. A New Series," vol. 26, pp. 3250–3253 (Sep. 1961).

Venkatasubramanian et al, "Synthesis and characterization of spinnable sol–gel derived polyborates," *Journal of Non–Crystalline Solids* 130 (1991) pp. 144–156, North Holland, no month.

Wade et al, "Synthesis of Fiber Forming Polyborates," *Polym. Mat. Sci–Eng.*, vol 64 (1991), pp. 377–378 no month.

Wade et al, "Boron Nitride Fibers From Polyborates," *Poly. Prepr.* (1991), 32(3), pp. 554–555 no month.

Venkatasubramanian et al, "Synthesis and Characterization of Spinnable Sol–Gel Derived Polyborates," *Polym. Mater. Sci. & Eng.*, vol 62 (1990) pp. 614–619; no month.

Zhang et al, "A Novel Electrolyte Solvent for Rechargeable Lithium and Lithium–Ion Batteries", *J. Electrochem. Soc.*, vol. 143, No. 12, Dec. 1996, pp. 4047–4053.

Quartarone et al, "Sol–Gel Synthesis, Thermal Characterization and Conductivity of New Glass–Polymer Solid Electrolytes," *Journal of Thermal Analysis*, vol. 47 (1996) pp. 235–245 no month.

Mehta et al, "Chemistry Letters," vol. 9, Jul. 31, 1997, pp. 915–916, XP002085988, Japan.

* cited by examiner

PMMA/Bx (3, 3, C14) electrolytes

Bx(3, 3, C14):LiCF$_3$SO$_3$=1:1

Un-plasticized sample:30%PMMA, 70%Bx(3, 3, C14)

30%PBMA/70%Bx (3, 3, C14) system

Bx(3, 3, C14):LiCF$_3$SO$_3$=1:1

IONICALLY CONDUCTING MOLECULE, IONIC CONDUCTOR AND PROCESS FOR PRODUCING THE SAME

BACKGROUND OF THE INVENTION

1. Field of the Invention

The present invention relates to an ionically conducting molecule and an ionic conductor which can be utilized as a solid conductor for a battery, and to a process for producing the ionic conductor.

2. Description of the Related Art

In general, since an ionically conducting polymer exhibits ease of processability into films, is lightweight and flexible, it is expected to find application in the field of electrochemistry, in particular in an all-solid lithium secondary battery.

There are several types of ionically conducting polymer. A single ion conducting polymer is a polymer in which only the cations act as charge carriers. A bi-ion conducting polymer is a polymer in which both the cations and the anions act as charge carriers. Single ion conducting polymers are preferable to bi-ion conductors for use in lithium secondary batteries for the following reasons. When a bi-ion conductor is used, the electrodes are blocking with respect to the anions. Thus, during charge and discharge processes, anions accumulate at the positive electrode which causes polarization of the conducting film. As a result of this phenomenon, the ionic conductivity decreases with time.

Therefore, in order to make an ionically conducting polymer into a single ion conductor, in which only the cations act as the charge carriers, it is necessary to fix the counter anion onto the ionically conducting polymer structure.

However, even in the aforementioned case, ion pairing of the cations with the fixed anions hinders movement of the former. Accordingly, mobility of the cation decreases and the ionic conductivity is greatly reduced.

The following methods have been thought of in order to reduce the influence of ion pairing. For example, the electron density on the anion is reduced by introduction of an electron withdrawing group; the cation is hindered stereochemically from approaching the anion by introduction of a bulky substituent group around the anion; and the distance between the fixed anions is shortened so as to reduce the activation energy barrier for cation motion.

For instance, Japanese Unexamined Patent Publication (KOKAI) No. 8-339,827 discloses the method for reducing charge density on the anion by introducing an electron withdrawing group. This idea is to fix the anion onto the polymer structure during polymer synthesis. Consequently, in order to synthesize the structure containing fixed anions, a complex synthetic route is necessary and the synthesis is difficult.

Japanese Unexamined Patent Publication (KOKAI) No. 10-223,258 discloses a non-aqueous lithium battery in which the ionic conductivity is improved by dissolution of a capacity attenuation inhibitor additive compound in the electrolyte. In this non-aqueous battery, the ionic conductivity is enhanced by using an organic solvent which takes part in the ionic conductivity and in which the capacity attenuation inhibitor additive compound is dissolved. Here, since the movement of the ions, which results in the ionic conductivity, is carried out in the organic solvent, the capacity attenuation inhibitor additive compound has a boroxine ring structure, which has a side chain composed of an alkyl group, so that it is likely to dissolve in the organic solvent.

In the lithium battery set forth in Japanese Unexamined Patent Publication (KOKAI) No. 10-223,258, the ionic conductivity is improved in the electrode member. However, only the conductivity of the electrolyte itself is upgraded. Hence, the ion conductivity of the ion conducting polymer is not enhanced.

SUMMARY OF THE INVENTION

It is therefore an object of the present invention to provide an ionically conducting molecule, an ionic conductor, which exhibits high mechanical strength and ionic conductivity, and a process for producing the same.

In order to carry out the object, the inventors of the present invention thought of preparing an ionically conducting molecule which both traps anions and provides an ion conducting pathway. They succeeded in obtaining an ionically conducting polymer which contains a boroxine ring for anion trapping and a molecular chain which provides an ion conducting pathway. Moreover, by using a structural member in which the tonically conducting molecule and salt are dispersed and immobilized, they successfully prepared an ionic conductor which is good in terms of mechanical strength and exhibits high ionic conductivity.

An ionically conducting molecule according to the present invention comprises:

a molecular chain which provides an ion conducting pathway; and a boroxine ring bonded to the molecular chain and trapping an anion.

An ionic conductor according to the present invention comprises:

an electrolyte salt for ionic conduction;

an ionically conducting molecule including a molecular chain which provides an ion conducting pathway and a boroxine ring bonded to the molecular chain and trapping anions resulting from the electrolyte salt; and a structural member for dispersion and immobilization of the ionically conducting molecule and the electrolyte salt.

A process for producing an ionic conductor according to the present invention comprises the steps of:

synthesis of an ionically conducting molecule including a molecular chain which provides an ion conducting pathway and a boroxine ring bonded to the aforementioned molecular chain and trapping anions; and dispersion and immobilization of the ionically conducting molecule and an electrolyte salt in a structural member by compounding the ionically conducting molecule, the electrolyte salt and the structural member.

The ionically conducting molecule according to the present invention increases the fraction of charge carried by cations because the boroxine rings trap the anions of the electrolyte salt. The behaviour of the ionic conductor approaches more closely that of a single ion conductor. Note, by using boroxine rings, we do not get a single ion conductor but due to the strong interaction between the anions and the boroxine ring, the mobility of the anions is reduced and therefore more of the charge is carried by cations. Namely, the behaviour of the ionic conductor more closely approaches that of a single ion conductor. Moreover, since the anion is trapped by way of interaction of electrons on the anion with the boroxine ring, there is a much smaller contribution of these anion electrons towards ion pairing with the cation. As a result, the ionic conductivity due to the cation is improved. In addition, in the ionic conductor according to the present invention, the structural member improves the mechanical strength of the ionic conductor.

The process for producing the ionic conductor according to the present invention comprises the step of synthesizing the aforementioned ionically conducting molecule, and the step of dispersion and immobilization of the ionically conducting molecule and the electrolyte salt in a structural member by compounding the ionically conducting molecule, the electrolyte salt and the structural member, thereby producing the ionic conductor. Moreover, when an annealing step is carried out after the dispersion and immobilization step, the ionic conductivity of the ionic conductor is enhanced.

The ionically conducting molecule according to the present invention has a boroxine ring structure, which is an electron pair acceptor working as a receptacle (anion trap) for anions, and a molecular chain which provides an ion conducting pathway, and which promotes conduction of the cations. Accordingly, the boroxine ring structure interacts strongly with the anionic electron pair of the electrolyte salt in the ionic conductor, thereby reducing the mobility of the anions and causing the ionically conducting system to exhibit a high cation transport number. Therefore, a cation transport number enhancement is observed, and this transport number can more closely approach 1.

The ionic conductor according to the present invention has the aforementioned tonically conducting molecule and an electrolyte salt for carrying out ionic conduction in the structural member. The structural member improves the mechanical strength of the ionic conductor. Consequently, the ionic conductor makes a tough, solid ionic conductor. Moreover, the present ionic conductor exhibits a small interfacial resistance between itself and metallic lithium, and the small interfacial resistance is stable with time. Therefore, there are great expectations of the present ionic conductor as a material for lithium batteries.

BRIEF DESCRIPTION OF THE DRAWINGS

A more complete appreciation of the present invention and many of its advantages will be readily obtained as the same becomes better understood by reference to the following detailed description when considered in connection with the accompanying drawings and detailed specification, all of which forms part of the disclosure.

DETAILED DESCRIPTION OF THE PREFERRED EMBODIMENTS

Figure 1:
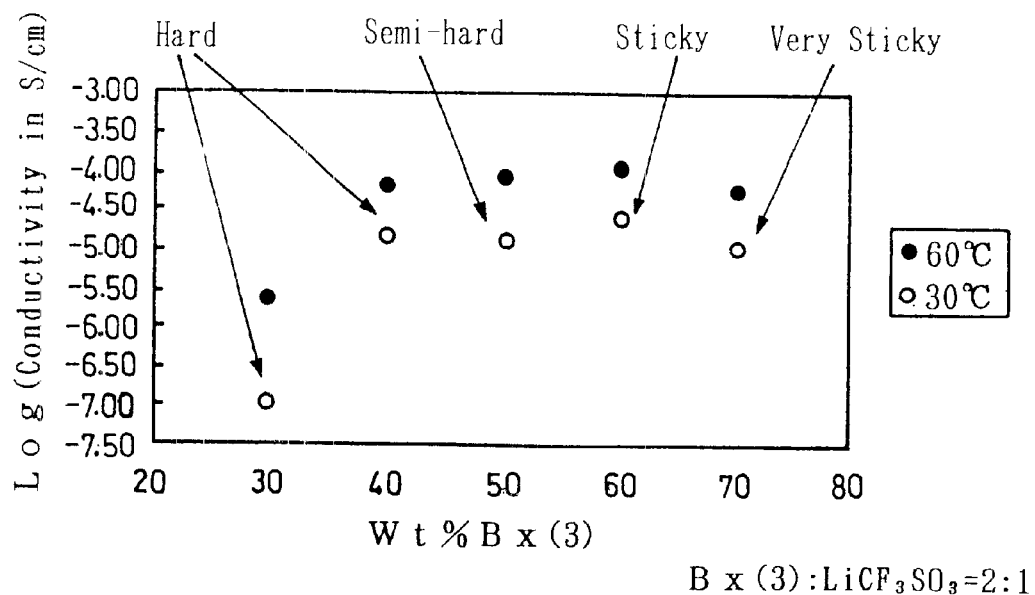
FIG. 1 is a diagram illustrating the relationship between the Bx(3) content and the ionic conductivity in an ionic conductor of Example No. 4.

Having generally described the present invention, a further understanding can be obtained by reference to the specific preferred embodiments which are provided herein for the purpose of illustration only and are not intended to limit the scope of the appended claims.

The ionically conducting molecule according to the present invention has a molecular chain which provides an ion conducting pathway and a boroxine ring. The ionically conducting molecule takes part in transporting the cation resulting from the electrolyte salt for ionic conduction. Namely, under the circumstance that the ionically conducting molecules are dispersed and immobilized in the structural member, the cations are transported in the ionic conductor.

The boroxine ring, which constitutes the ionically conducting molecule, captures the anion resulting from the electrolyte salt for ionic conduction. Namely, since the ionically conducting molecule captures the anion, the mobility of the anion is greatly reduced. Furthermore, dissociation of the cation and anion is enhanced and motion of the cation is facilitated. Thus the cation transport number of the ionic conductor is enhanced.

It is preferred that the boroxine ring structure can be trialkoxy boroxine. Namely, trialkoxy boroxine has a boroxine ring $((BO)_3)$. The boroxine ring captures the anion, and the alkoxy groups connected to the boroxine ring are used to transfer the cation.

The molecular chain which provides an ion conducting pathway in the ionically conducting molecule can preferably be a molecule having an ether chain. The lone pairs of electrons on the oxygen forming the ether bond in the ether chain are used to transfer the cation. Hence, regardless of the materials of the structural member, the ionically conducting molecule imparts ion conducting capability to the ionic conductor.

It is preferred that the ether chain can be ($—CH_2—CH_2—O—$).

It is preferred that the ionically conducting molecule can exhibit compatibility between itself and the structural member. When the ionically conducting molecule exhibits compatibility between itself and the structural member, the ionically conducting molecules can be uniformly dispersed and immobilized in the structural materials without causing phase separation.

It is possible to introduce an alkyl group, which does not take part in ion conduction, into the boroxine ring structure. By the introduction of the alkyl group, the resulting ionically conducting molecules assemble with each other.

The ionic conductor according to the present invention comprises the electrolyte salt for ionic conduction, the ionically conducting molecule, and the structural member.

It is preferred that the ionically conducting molecule can exhibit compatibility between itself and the structural member. When the ionically conducting molecule exhibits compatibility between itself and the structural member, the ionically conducting molecules can be uniformly dispersed and immobilized in the structural member without causing phase separation.

The electrolyte salt for ionic conduction is an ion source in the ionic conductor so that the ionic conductor exhibits ionic conductivity. Namely, the electrolyte salt dissociates into anions and cations in the ionic conductor. The resulting ions are transported so that ionic conductivity is exhibited by the ionic conductor.

It is preferred that the electrolyte salt for ionic conduction can be a lithium salt. When a lithium salt is used as the electrolyte salt, an ionic conductor with a high cation transport number is prepared, that is to say that a high proportion of the charge is carried by the lithium ions. As for such a lithium salt, it is possible, for example to list lithium salts such as $Li(CF_3SO_2)_2 N$, $LiCF_3SO_3$, $LiBF_4$, LiBr, LiCl and $LiPF_6$.

The structural member disperses and immobilizes the ionically conducting molecules and the electrolyte salt for ionic conduction in the ionic conductor. Namely, by dispersing and immobilizing the ionically conducting molecules which provide an ion conducting pathway and the electrolyte salt in the ionic conductor, the ionic conductor can exhibit ionic conductivity. The dispersion and immobilization of the ionically conducting molecules and the electrolyte salt herein means a state that the ionically conducting molecules and the electrolyte salt exist in the structural member without reacting with the structural member. Moreover, the structural member gives mechanical strength to the ionic conductor. Accordingly, it is preferred that the structural member can include polymers, which do not react with the ionically conducting molecules and electrolyte salt, and porous substances.

It is preferred that the structural member can be at least one member selected from the group consisting of ethylene oxide-propylene-oxide copolymer, poly(methyl methacrylate), poly(oligoethylene glycol methacrylate), poly(vinyl chloride), bentonite, cellulose acetate, poly(vinylidene fluoride-hexafluoropropylene) copolymer. In the ionic conductor according to the present invention, since the ionically conducting molecule provides an ion conducting pathway, the structural member does not particularly require an ion transfer function of its own.

In the ionic conductor according to the present invention, the amounts of the ionically conducting molecule and the electrolyte salt cannot be determined explicitly because they depend on the materials of the structural member.

In the ionic conductor according to the present invention, since there exist boroxine rings in appropriate amounts working as anion traps, the anion traps capture anions from the electrolyte salt. Thus, it is possible to obtain an ionic conductor in which most of the charge is carried by the cations. The behaviour of the conductor approaches that of a single (cation) ion conductor. Since the anion traps formed in the ionic conductor do not hinder the motion of the cations by way of the ether chains and ion pairing between the cation and anion is reduced as a result of anion trapping by the boroxine rings, the conductivity due to cation motion is enhanced.

The ionic conductor according to the present invention can preferably be annealed. This heat treatment improves the ionic conductivity.

The ionic conductor according to the present invention has the extremely favourable characteristic that it exhibits an extremely small interfacial resistance between itself and metallic lithium. This characteristic means that the internal resistance can be reduced when the present ionic conductor is used as a solid electrolyte in lithium batteries using metallic lithium.

The trialkoxy boroxine compound, working as the ionically conducting molecule, can preferably be prepared in the following manner. For instance, boric acid ($B(OH)_3$) and poly(ethylene glycol) monomethyl ether (PEGMME) are reacted in the presence of an acid catalyst, thereby generating an ester of boric acid ($B(OR)_3$). Three mol equivalents of PEGMME are used for each equivalent of $B(OH)_3$. The $B(OR)_3$ and boric oxide ($B_2O_3$) are heated in a dry nitrogen atmosphere, thereby producing the trialkoxy boroxine compound. Molar equivalents of $B(OR)_3$ and boric oxide ($B_2O_3$) are used to prepare the trialkoxy boroxine compound. Since the trialkoxy boroxine compound is prepared by a process via the ester of boric acid, the trialkoxy boroxine compound can be obtained in high purity and free from residual hydroxy groups. On the other hand, when the trialkoxy boroxine compound is prepared by direct reaction of PEGMME and boric oxide, small traces of unreacted hydroxy groups may remain in the resulting trialkoxy boroxine compound, and such a trialkoxy boroxine compound will exhibit reduced electrochemical stability compared to the pure compound.

An asymmetric boroxine compound can be prepared in the following manner. For example, an ester of boric acid is prepared by the reaction of boric acid with an excess of alcohol. The asymmetric boroxine compound can then be prepared by reaction of two or more different esters of boric acid with boric oxide. In this process, stoichiometric quantities of the reagents are used. For instance, two esters of boric acid are mixed in a molar ratio of 2:1, and are reacted with 3 mol of boric oxide. Thus, an asymmetric boroxine compound can be obtained by such a stoichiometric reaction.

The other process for producing an asymmetric boroxine compound is carried out in the following manner. An asymmetric ester of boric acid is prepared in advance, and is reacted with an equal molar quantity of boric oxide.

Hereinafter, the present invention will be described with reference to specific examples.

First of all, examples of the present ionically conducting molecule will be described.

EXAMPLE NO. 1

A trialkoxy boroxine compound (Bx(n)), Example No. 1 of the present ionically conducting molecule, had a structure as illustrated by the following structural formula (1), and was produced as illustrated in the following chemical equation (2).

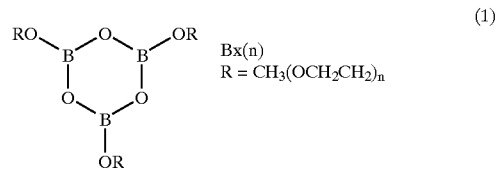

(1)

Bx(n)
R = $CH_3(OCH_2CH_2)_n$

-continued

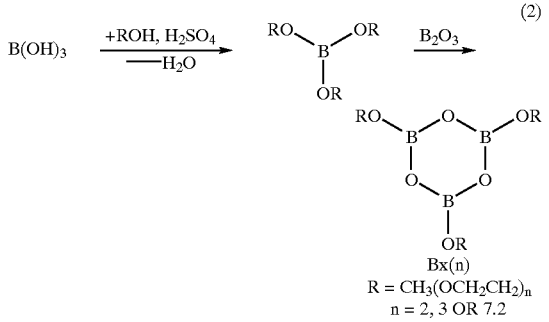

First, boric acid (B(OH)$_3$) and poly(ethylene glycol) monomethylether (PEGMME) were reacted in refluxing toluene in the presence of a sulfuric acid catalyst. 3 mol equivalents of PEGMME was used for each mol equivalent of B(OH)$_3$. During this process, the water produced in the reaction was removed using a Dean-Stark apparatus. After completion of the reaction, the sulfuric acid was neutralized by potassium carbonate (K$_2$CO$_3$). Thereafter, the ester of boric acid (B(OR)$_3$) was isolated by vacuum distillation.

Subsequently, the resultant B(OR)$_3$ was mixed with an equivalent number of mols of boric oxide (B$_2$O$_3$). The mixture was then heated under dry nitrogen. Thus, the trialkoxy boroxine compound (Bx(n)) of Example No. 1 was prepared.

EXAMPLE NO. 2

In Example No. 2, an asymmetric trialkoxy boroxine compound, used as an ionically conducting molecule and containing a variety of different alkoxy groups, could be produced by way of the reaction process illustrated in the following chemical equation (3).

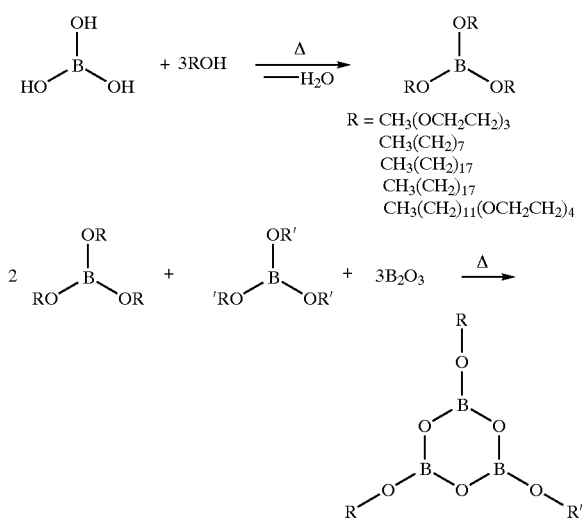

In the production process, boric acid B(OH)$_3$ and an excess of alcohol were heated and refluxed in toluene for 6 hours. The resulting water was removed by azeotropic distillation in a Dean-Stark apparatus. Subsequently, esters of boric acid were obtained by distillation. The esters of boric acid thus obtained were mixed in a molar ratio of 2:1. 3 mols of boric oxide were added to the reaction mixture containing 3 mols of the esters of boric acid (in a ratio of 2:1). The mixture was then heated at 60° C. for 48 hours. Thus, an asymmetric boroxine compound of Example No. 2 having two different alkoxy groups was prepared.

EXAMPLE NO. 3

In Example No. 3, an asymmetric trialkoxy boroxine compound, used as an ionically conducting molecule and containing a variety of different alkoxy groups, could be produced by way of the reaction process illustrated in the following chemical equation (4).

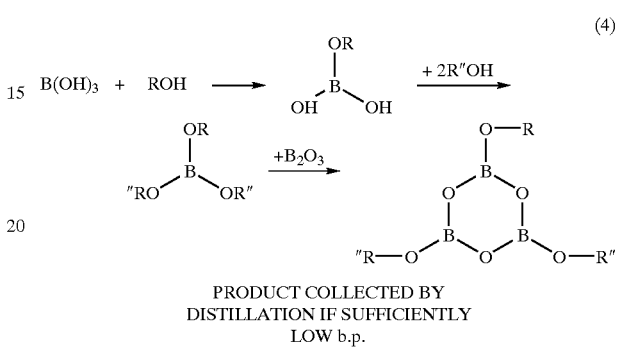

In the production process, first, equal molar amounts of boric acid B(OH)$_3$ and an alcohol were heated and refluxed in toluene for 6 hours. The resulting water was removed by azeotropic distillation in a Dean-Stark apparatus. Subsequently, 2 mol equivalents of oligoethylene glycol monomethylether was added to the mixture. The mixture was heated and refluxed in toluene, thereby producing asymmetric esters of boric acid. The asymmetric esters of boric acid exhibiting low boiling points were isolated by distillation. Then, an equal number of mols of boric oxide (B$_2$O$_3$) was added to the asymmetric esters of boric acid. Thereafter, the mixture was heated to 70° C. for 36 hours. Thus, an asymmetric boroxine compound of Example No. 3 was prepared.

Then, by using the ionically conducting molecules prepared in Example No. 1 through Example No. 3, ionic conductors according to the present invention were produced and are described in the following examples. The ionic conductors prepared in the following examples were formed as a film.

EXAMPLE NO. 4

In Example No. 4, an ethylene oxide-propylene oxide (EO-PO) copolymer was used as the structural material, the boroxine compound (Bx(n), B$_3$O$_3$[(OCH$_2$CH$_2$)$_n$OCH$_3$]$_3$) prepared in Example No. 1 was used as the ionically conducting molecule, and LiCF$_3$SO$_3$ was used as the electrolyte salt for ionic conduction. Namely, in the ionic conductor of Example No. 4, the Bx(n) and LiCF$_3$SO$_3$ were dispersed and immobilized in the EO-PO copolymer.

In the samples of the ionic conductors of Example No. 4, the ratio of EO-PO copolymer and ionically conducting molecule (Bx(n)) as well as the length of the side chains in Bx(n), namely, n in B$_3$O$_3$[(OCH$_2$CH$_2$)$_n$OCH$_3$]$_3$ were varied.

As samples of Example No. 4, ionic conductors having compositions set forth in Table 1 below were prepared, and included EO-PO copolymer, Bx(3), Bx(7.2) and the salt LiCF$_3$SO$_3$. The EO-PO copolymer was composed of EO and PO in the molar ratio 80:20. The weight percentages of the Bx(n) in Table 1 were the weights of Bx(n) with respect to the total weight of EO-PO copolymer and Bx(n). The $LiCF_3SO_3$ contents were as follows: namely; when Bx(7.2) was used, the molar ratio of C—O—C in the Bx(7.2) to $LiCF_3SO_3$ was 20:1; and when Bx(3) was used, the molar ratio of Bx(3) to $LiCF_3SO_3$ was 2:1.

TABLE 1

| Sample I.D. | Bx(n) | Bx(n) (wt. %) | $\sigma$ (30° C.) ($Scm^{-1}$) | $\sigma$ (60° C.) ($Scm^{-1}$) | Film State |
|---|---|---|---|---|---|
| 1 | Bx(7.2) | 30 | $1.5 \times 10^{-5}$ | $7.1 \times 10^{-5}$ | Hard Film |
| 2 | Bx(7.2) | 40 | $\sim 1.3 \times 10^{-5}$ | $5.2 \times 10^{-5}$ | Hard Film |
| 3 | Bx(7.2) | 50 | $\sim 2.0 \times 10^{-5}$ | $1.2 \times 10^{-4}$ | Semi-hard Film |
| 4 | Bx(3) | 30 | $4.6 \times 10^{-6}$ | $4.6 \times 10^{-5}$ | Hard Film |
| 5 | Bx(3) | 50 | $1.9 \times 10^{-5}$ | $7.7 \times 10^{-5}$ | Semi-hard Film |
| 6 | Bx(3) | 70 | $1.3 \times 10^{-5}$ | $4.7 \times 10^{-5}$ | Very Sticky Film |

Subsequently, as other samples of Example No. 4, ionic conductors having compositions set forth in Table 2 were prepared, and included EO-PO copolymer, Bx(3) and $LiCF_3SO_3$. The EO-PO copolymer was composed of EO and PO in the molar ratio of 90:10. Here, in Table 2, the weight percentage of Bx(3) was calculated in the same manner as described in Table 1, and the molar ratio of Bx(3) to $LiCF_3SO_3$ was the same as in Table 1, for example, the molar ratio Bx(3):$LiCF_3SO_3$=2:1.

TABLE 2

| Sample I.D. | Bx(n) (wt. %) | $\sigma$ (30° C.) ($Scm^{-1}$) | $\sigma$ (60° C.) ($Scm^{-1}$) | Film State |
|---|---|---|---|---|
| 7 | 30 | $1.1 \times 10^{-7}$ | $2.3 \times 10^{-6}$ | Hard Film |
| 8 | 40 | $1.4 \times 10^{-5}$ | $6.9 \times 10^{-5}$ | Hard Film |
| 9 | 50 | $1.3 \times 10^{-5}$ | $8.1 \times 10^{-5}$ | Semi-hard Film |
| 10 | 60 | $2.4 \times 10^{-5}$ | $1.1 \times 10^{-4}$ | Sticky Film |
| 11 | 70 | $1.1 \times 10^{-5}$ | $5.5 \times 10^{-5}$ | Very Sticky Film |

These samples of the ionic conductors of Example No. 4 were produced in the following manner. For instance, the EO-PO copolymer, Bx(n) and $LiCF_3SO_3$ were dissolved in THF (tetrahydrofuran). Thereafter, the THF was removed by distillation. (Evaluation)

In order to assess the samples as ionic conductors, the ionic conductivity was measured. Note that the ionic conductivity measurements were carried out at 30° C. and 60° C. Table 1 and Table 2 also summarize the results of the conductivity measurements of the samples. In addition, the variation of ionic conductivity with Bx(3) content of samples of ionic conductors which included the EO-PO copolymer with an EO:PO molar ratio of 90:10 was determined. The relationships between the logarithmic values of the ionic conductivities and the Bx(3) contents are illustrated in FIG. 1.

According to Table 1, the ionic conductivities did not depend greatly on the quantity of added Bx(n) and the samples exhibited relatively high ionic conductivity values. Moreover, in the EO-PO copolymer system, the samples exhibited flow as the temperature was greatly increased. However, it is possible to obtain a polymer electrolyte which exhibits high ionic conductivity and favourable mechanical properties by varying the structural member and the length of the ether side chains bonded to the boroxine ring.

According to Table 2 and FIG. 1, the samples of the ionic conductors of Example No. 4 exhibited quite high conductivities. Further, the ionic transport number of the lithium ion ($Li^+$) was 0.35. Furthermore, an ionic conductor of the EO-PO copolymer system exhibited a large interfacial resistance between itself and lithium metal. However, addition of Bx(n) resulted in a reduction of this interfacial resistance by a factor of about 1/60.

EXAMPLE NO. 5

In Example No. 5, poly(methyl methacrylate) (PMMA) was used as the structural member, the boroxine compound (Bx(n)) prepared in Example No. 1 was used as the ionically conducting molecule, and $LiCF_3SO_3$ was used as the electrolyte salt for ionic conduction. Namely, in the ionic conductor of Example No. 5, the Bx(n) and $LiCF_3SO_3$ were dispersed and immobilized in the PMMA. Note that, in the ionic conductors of Example No. 5, the length of ether side chains on the boroxine ring compound, namely, n in $B_3O_3$ $[(OCH_2CH_2)_nOCH_3]_3$, were varied.

The ionic conductors of Example No. 5 were comprised of PMMA, Bx(3) and $LiCF_3SO_3$. Table 3 summarizes the weight percentages of Bx(3), the ionic conductivities and the state of the ionic conductors of Example No. 5. Here, the weight percentages of Bx(3) in Table 3 were the weights of Bx(3) with respect to the total weights of PMMA and Bx(3). The content of $LiCF_3SO_3$ was fixed so that the molar ratio of Bx(3):$LiCF_3SO_3$ was 2:1.

TABLE 3

| Sample I.D. | Bx(n) (wt. %) | $\sigma$ (30° C.) ($Scm^{-1}$) | $\sigma$ (60° C.) ($Scm^{-1}$) | $\sigma$ (80° C.) ($Scm^{-1}$) | Film State |
|---|---|---|---|---|---|
| 12 | 60 | $5.8 \times 10^{-7}$ | $1.3 \times 10^{-5}$ | $2.9 \times 10^{-5}$ | Hard Sticky Solid |
| 13 | 70 | $4.2 \times 10^{-6}$ | $2.8 \times 10^{-5}$ | $6.6 \times 10^{-5}$ | Hard Sticky Solid |
| 14 | 78 | $1.2 \times 10^{-5}$ | $6.6 \times 10^{-5}$ | $1.4 \times 10^{-4}$ | Soft Sticky Semi-solid |
| 15 | 80 | $2.8 \times 10^{-5}$ | $1.4 \times 10^{-4}$ | $2.8 \times 10^{-4}$ | Very Sticky Liquid |

Here, these samples of the ionic conductors of Example No. 5 were produced in the same manner as those of Example No. 4. Namely, the PMMA, Bx(3) and $LiCF_3SO_3$ were dissolved in THF. Thereafter, the THF was removed from the solution by distillation.
(Evaluation)

In order to assess the samples of Example No. 5 as ionic conductors, the ionic conductivities were measured. Note that the ionic conductivity measurements were carried out at temperatures of 30° C., 60° C. and 80° C. Table 3 summarizes the results of the measurements.

According to Table 3, the ionic conductivities increased with the proportion of Bx(3) in PMMA. However, when the Bx(3) content was too large, the ionic conductor could not maintain the solid state. Note that the ionic conductivity varied only slightly with temperature.

Figure 2:
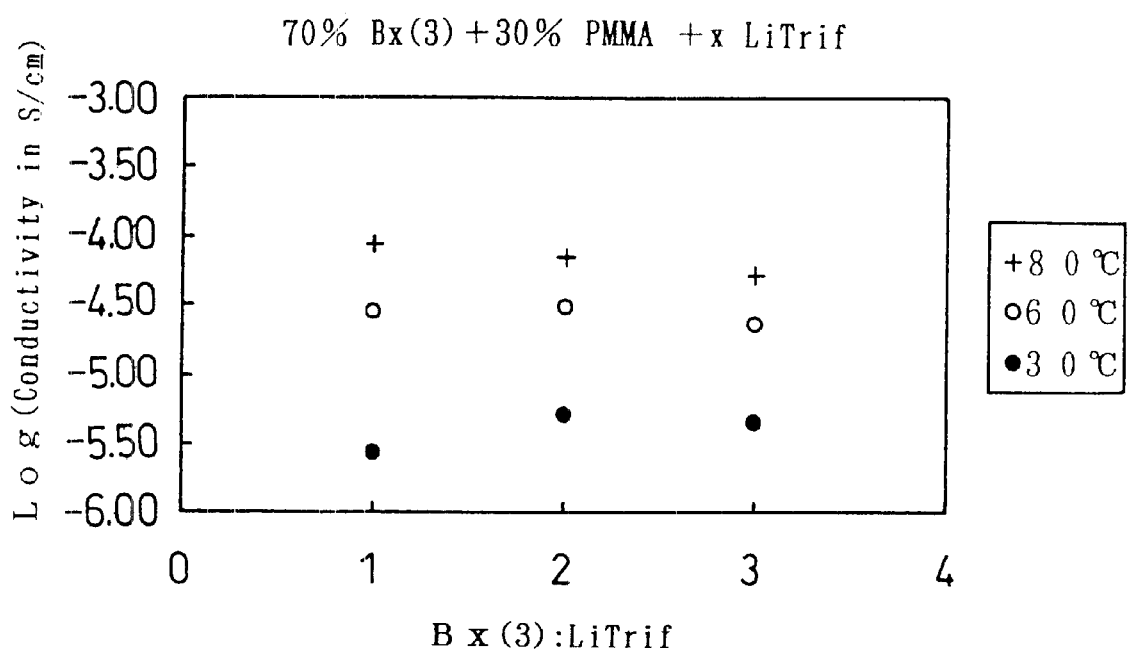
FIG. 2 is a diagram illustrating the relationship between the Li ion content and the ionic conductivity in an ionic conductor of Example No. 5.

In Table 3, Sample No. 13 is listed which contained 70 weight % of Bx(3). The variation of ionic conductivity of Sample No. 13 with $LiCF_3SO_3$ content was measured. The results are illustrated in FIG. 2. Note that the $LiCF_3SO_3$ content was varied by changing the molar ratio of Bx(3): $LiCF_3SO_3$. Here, the result of the measurements illustrated in FIG. 2 show the relationship between the logarithmic values of the ionic conductivities and the amounts of added Bx(3).

According to FIG. 2, the ionic conductivities of the samples of the ionic conductors varied only slightly with the molar ratio Bx(3):$LiCF_3SO_3$. When the molar ratio Bx(3): $LiCF_3SO_3$ was small, namely, for high Li salt concentrations, the samples of the ionic conductors were more rigid. In addition, when the molar ratio was varied, the ionic conductivities varied only slightly with temperature.

Briefly, the original Sample No. 13 included 30 weight % PMMA and 70 weight % Bx(3), and the molar ratio Bx(3):LiCF$_3$SO$_3$ was 2:1. The cationic transport number of Sample No. 13 was measured using the ac impedance/dc polarization method. As a result, the Li$^+$ transport number (t$^+$) was approximately 0.8 at 31° C. Thus, Sample No. 13 was proved to exhibit an extremely high Li$^+$ transport number and behaviour approaching that of a single ion conductor in which the mobility of the anions was greatly inhibited.

Accordingly, even when PMMA, which contains no ether chains, was used, it was found that an anion trapping ionic conductor could be obtained.

As a modified version of Example No 5, samples of the ionic conductor were prepared, and included Bx(2), Bx(3) and Bx(7.2) which contained ether side chains in the boroxine compound with 2, 3, and 7.2 ethylene oxide units respectively. Namely, n in B$_3$O$_3$[(OCH$_2$CH$_2$)$_n$OCH$_3$]$_3$ was varied to be 2, 3 and 7.2. Here, the Bx(n) content was varied. Similarly to Bx(3) in Example Nos. 4,5 and 6 set forth in Table 1, the LiCF$_3$SO$_3$ content, for example, the molar ratio of Bx(3):LiCF$_3$SO$_3$ was fixed at 2:1.

(Evaluation)

Figure 3:
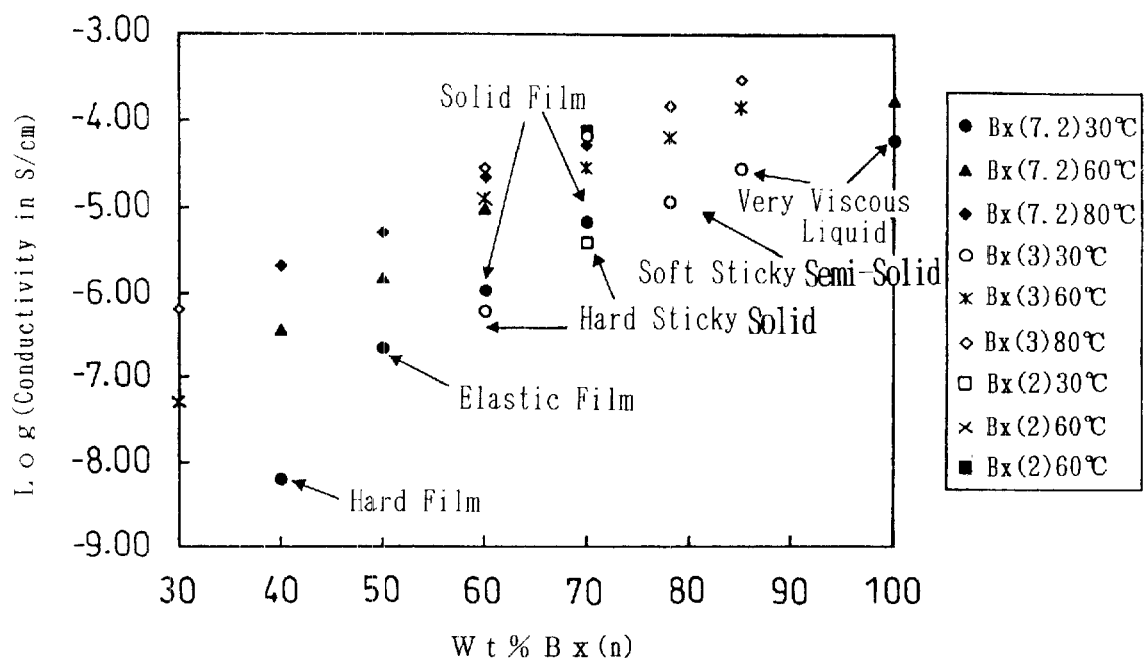
FIG. 3 is a diagram illustrating the relationship between the Bx(n) content and the ionic conductivity in an ionic conductor of Example No. 5.

In order to assess these samples as ionic conductors, the ionic conductivities were measured. The results of the measurements are illustrated in FIG. 3. Note that, in FIG. 3, the horizontal axis specifies the Bx(n) content and the vertical axis specifies the logarithmic values of the ionic conductivities.

According to FIG. 3, when the Bx(n) content was 60 weight % or more, the samples of Example No. 5 exhibited sufficiently high ionic conductivities. However, when the Bx(n) content exceeded 85 weight %, the samples were less likely to maintain the solid state.

EXAMPLE NO. 6

An ionic conductor of Example No. 6 was an ionic conductor which included poly(oligothylene glycol methacrylate) (PM4), Bx(n) and LiCF$_3$SO$_3$. Namely, in the ionic conductor of Example No. 6, the Bx(n) and LiCF$_3$SO$_3$ were dispersed and immobilized in the PM4. A variety of samples of the ionic conductors of Example No. 6 were prepared by varying the content of Bx(n).

The samples of the ionic conductor of Example No. 6 included Bx(3) in amounts varying from 20 to 50 weight %. Here the weight percentages of the Bx(3) were the weights of Bx(3) with respect to the total weight of PM4 and Bx(3). The LiCF$_3$SO$_3$ content was such that the molar ratio of C—O—C in the Bx(3) side chains to LiCF$_3$SO$_3$ was 20:1, i.e., C—O—C:LiCF$_3$SO$_3$ was 20:1.

As a modified version of Example No. 6, samples of the ionic conductor were prepared which were comprised of PM4, Bx(7.2) and LiCF$_3$SO$_3$. Note that the samples contained Bx(7.2) in amounts varying from 0 to 100%. The LiCF$_3$SO$_3$ content, for example, the molar ratio of Bx(7.2):LiCF$_3$SO$_3$ was 2:1.

The ionic conductor of Example No. 6 was produced by polymerizing a monomer in the presence of LiCF$_3$SO$_3$ and Bx(n). Namely, to a mixture of PM4 monomer, LiCF$_3$SO$_3$ and Bx(n), azobsisobutyronitrile (AIBN), an initiator, was added to initiate the polymerization. Thus, the ionic conductor could be produced. The production process is illustrated in the following chemical equation (5). The structure of PM4 is illustrated in the following structural formula (6).

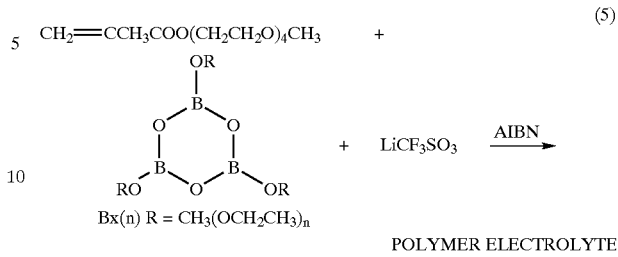

(5)

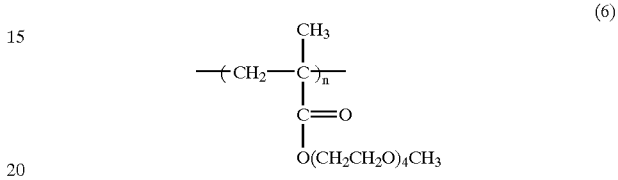

(6)

(Evaluation)

Figure 4:
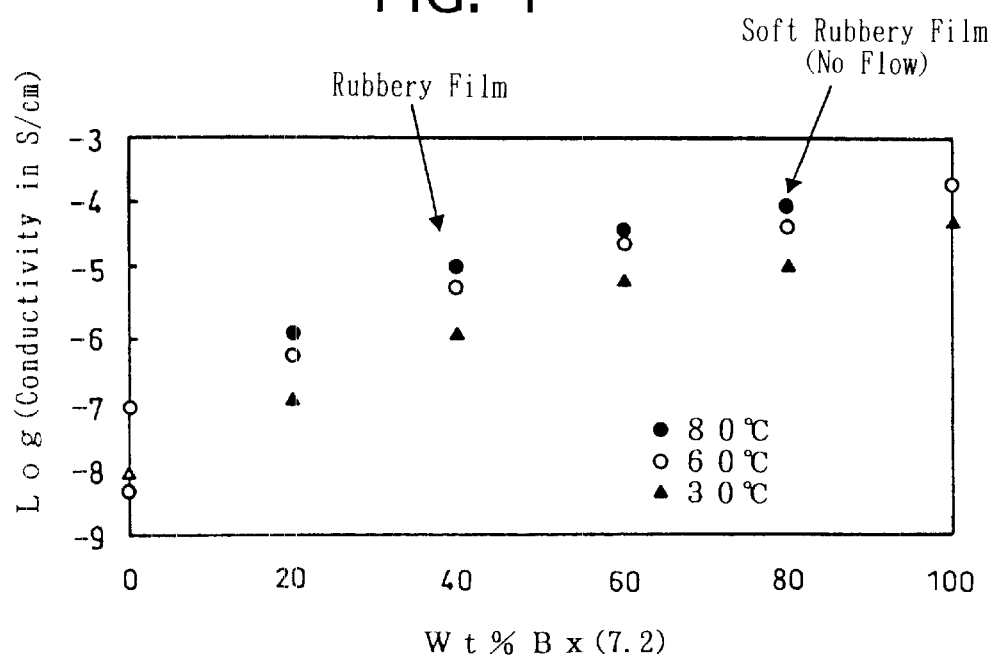
FIG. 4 is a diagram illustrating the relationship between the Bx(n) content and the ionic conductivity in an ionic conductor of Example No. 6.

In order to assess these samples as ionic conductors, the ionic conductivities of the ionic conductors of Example No. 6 were measured. Note that the ionic conductivity measurements were carried out at temperatures of 30° C., 60° C. and 80° C. The results of the measurements are illustrated in FIG. 4. FIG. 4 shows the relationship between the logarithmic values of the ionic conductivities and the Bx(7.2) contents.

The samples of the ionic conductors containing Bx(3) exhibited ionic conductivities of the order of 10$^{-5}$ S/cm at room temperature and 10$^{-4}$ S/cm at 60° C. However, these ionic conductors were viscous products, probably because their molecular weights were small.

According to FIG. 4, the samples of the ionic conductors of Example No. 6 exhibited remarkably high ionic conductivities. Ionic conductivity increased as the amount of added Bx(7.2) increased. Note that when 80 weight % Bx(7.2) was added, the samples showed conductivity which was close to the ionic conductivity of the liquid.

EXAMPLE NO. 7

Example No. 7 was an ionic conductor which was comprised of poly(vinyl chloride) (PVC), working as the structural member, Bx(n) and LiCF$_3$SO$_3$. More particularly, the ionic conductor of Example No. 7 was an ionic conductor containing Bx(3), where the boroxine compound Bx(3) contained ether side chains containing 3 ethylene oxide units, namely, n in B$_3$O$_3$[(OCH$_2$CH$_2$)$_n$OCH$_3$]$_3$ was equal to 3 and LiCF$_3$SO$_3$ in PVC. Table 4 sets forth the composition of the samples of ionic conductor of Example No. 7.

TABLE 4

| | Composition | |
|---|---|---|
| | (g) | (wt %) |
| Pvc | 413 | 51.5 |
| Bx(3) | 331 | 41.3 |
| Li Salt | 57.4 | 7.2 |

The sample of the ionic conductor No. 7 was prepared in the same manner as the production processes for Example No. 4 and Example No. 5. Namely, the PVC, Bx(3) and LiCF$_3$SO$_3$ were dissolved in THF. Thereafter, the THF was removed by distillation. The samples of ionic conductors of example No. 7. were thus prepared.

(Evaluation)

In order to assess the ionic conductors of Example No. 7, the ionic conductivities of the samples were measured. The results of the measurements are set forth in Table 5. Table 5 summarizes the ionic conductivities of the sample at temperatures of 25° C., 60° C. and 80° C.

TABLE 5

|  | σ (25° C.) (Scm$^{-1}$) | σ (60° C.) (Scm$^{-1}$) | σ (80° C.) (Scm$^{-1}$) |
| --- | --- | --- | --- |
| Results of Measurement | 3 × 10$^{-7}$ | 4.4 × 10$^{-7}$ | 1.3 × 10$^{-6}$ |

According to Table 5, it can be seen that the sample of the ionic conductor of Example No. 7 exhibited sufficiently high ionic conductivities. In addition, the sample of the ionic conductor of Example No. 7 was formed as a uniform film, and exhibited adequate strength.

EXAMPLE NO. 8

Example No. 8 was an ionic conductor which was comprised of bentonite, Bx(n) and LiCF$_3$SO$_3$. More particularly, the ionic conductor of Example No. 8 employed bentonite as the structural member. The ionic conductor contained Bx(3), where the boroxine compound Bx(3) contained ether side chains containing 3 ethylene oxide units, namely, n in B$_3$O$_3$[(OCH$_2$CH$_2$)$_n$OCH$_3$]$_3$ was equal to 3. Table 6 sets forth the composition of the sample of the ionic conductor of Example No. 8.

TABLE 6

|  | Composition | |
| --- | --- | --- |
|  | (g) | (wt %) |
| Bentonite | 212 | 51.5 |
| Bx(3) | 167 | 40.6 |
| Li Salt | 32.7 | 7.9 |

The sample of the ionic conductor of Example No. 8 was produced in the following manner. Predetermined amounts of bentonite powder, Bx(n) and the LiCF$_3$SO$_3$ were mixed together. Thereafter, the mixture was transferred in a mold, and was pressed manually. In the sample of the ionic conductor of Example No. 8, the bentonite particles and the Bx(3) were unevenly dispersed. In addition, since the ionic conductor of Example No. 8 was formed by pressing, there was room for improving the mechanical strength of the sample.

(Evaluation)

In order to assess the ionic conductors of Example No. 8, the ionic conductivities of the samples were measured. The sample of ionic conductor of Example No. 8 exhibited ionic conductivity of 3.7×10$^{-7}$ Scm$^{-1}$ at 25° C.

EXAMPLE NO. 9

Example No. 9 was an ionic conductor, which was comprised of cellulose acetate, a mixture of ethylene carbonate (EC) and propylene carbonate (PC), Bx(n) and LiCF$_3$SO$_3$. More particularly, the ionic conductor employed the cellulose acetate as the structural member. The ionic conductor contained Bx(3), where the boroxine compound Bx(3) contained ether side chains containing 3 ethylene oxide units, namely, n in B$_3$O$_3$[(OCH$_2$CH$_2$)$_n$OCH$_3$]$_3$ was equal to 3. Table 7 sets forth the composition of the sample of the ionic conductor of Example No. 9. Here, the mixing ratio of EC and PC was 1:1 by volume.

Note that the ionic conductor of Example No. 9 was prepared by mixing the cellulose acetate, the mixture of EC and PC, Bx(3) and the LiCF$_3$SO$_3$ with ultrasonic waves.

TABLE 7

|  | Composition | |
| --- | --- | --- |
|  | (g) | (wt %) |
| Cellulose Acetate | 0.213 | 17.0 |
| Bx(3) | 0.225 | 17.9 |
| Li Salt | 0.0613 | 4.9 |
| EC-PC | 0.745 | 60.2 |

(Evaluation)

In order to assess the ionic conductors of Example No. 9, the ionic conductivities of the samples were measured. The sample of ionic conductor of Example No. 9 exhibited ionic conductivity of 9.8×10$^{-5}$ Scm$^{-1}$ at 25° C.

EXAMPLE NO. 10

Example No. 10 was an ionic conductor which was comprised of poly(vinylidene fluoride-co-hexafluoropropylene) (PVdF-HFP), Bx(n) and LiCF$_3$SO$_3$. More particularly, the ionic conductor employed the poly (vinylidene fluoride-co-hexafluoropropylene), as the structural member. The ionic conductor contained Bx(3), where the boroxine compound Bx(3) contained ether side chains containing 3 ethylene oxide units, namely, n in B$_3$O$_3$ [(OCH$_2$CH$_2$)$_n$OCH$_3$]$_3$ was equal to 3. Table 8 sets forth the composition of the sample of the ionic conductor of Example No. 10.

The sample of the ionic conductor of Example No. 10 was prepared in the following manner. Namely, the poly (vinylidene fluoride-co-hexafluoropropylene), Bx(3) and LiCF$_3$SO$_3$ were dissolved in THF. Thereafter, the THF was removed from the sample mixture by distillation, and thereby the sample of the ionic conductor of Example No. 10 was prepared.

TABLE 8

|  | Composition | |
| --- | --- | --- |
|  | (g) | (wt %) |
| (PVdF-HFP) | 3.29 | 36.5 |
| Bx(3) | 5.03 | 55.9 |
| Li Salt | 0.68 | 7.6 |

(Evaluation)

In order to assess the ionic conductors of Example No. 10, the ionic conductivities of the samples were measured. The sample of ionic conductor of Example No. 10 exhibited high ionic conductivities, of 2.0×10$^{-6}$ Scm$^{-1}$ at 30° C. and 1.6×10$^{-5}$ Scm$^{-1}$ at 60° C.

The resulting ionic conductors were examined in order to see how an annealing treatment influenced the temperature dependency of the ionic conductivities in the following examples.

EXAMPLE NO. 11

A mixture was prepared in which an ionically conducting molecule Bx(3) and an ethylene oxide-propylene oxide copolymer were mixed. The ionically conducting molecule Bx(3) was the same as the Bx(n) prepared in Example No. 1, and was included in an amount of 60% by weight. The ethylene oxide-propylene oxide copolymer included EO and PO in a ratio of 90:10 by mol (i.e., EO:PO=90:10 by mol), and was included in an amount of 40% by weight. Then, $LiCF_3SO_3$ (LiTrif), the electrolyte salt for ionic conduction, was added to the mixture in an equal molar amount to that of the Bx(3). Thereafter, the ionic conductor mixture was processed into a film in the same manner as Example No. 4. This ionic conductor was labeled as an un-annealed sample of Example No. 11. The ionic conductor was then heated at 90° C. for 2 hours, was cooled slowly to 35° C. over a period of 4 hours, and was left at room temperature for 15 hours or more. Thus, an annealed sample 1 was obtained. The annealing treatment was carried out twice. Thus, a twice-annealed sample 2 was obtained.

Figure 5:
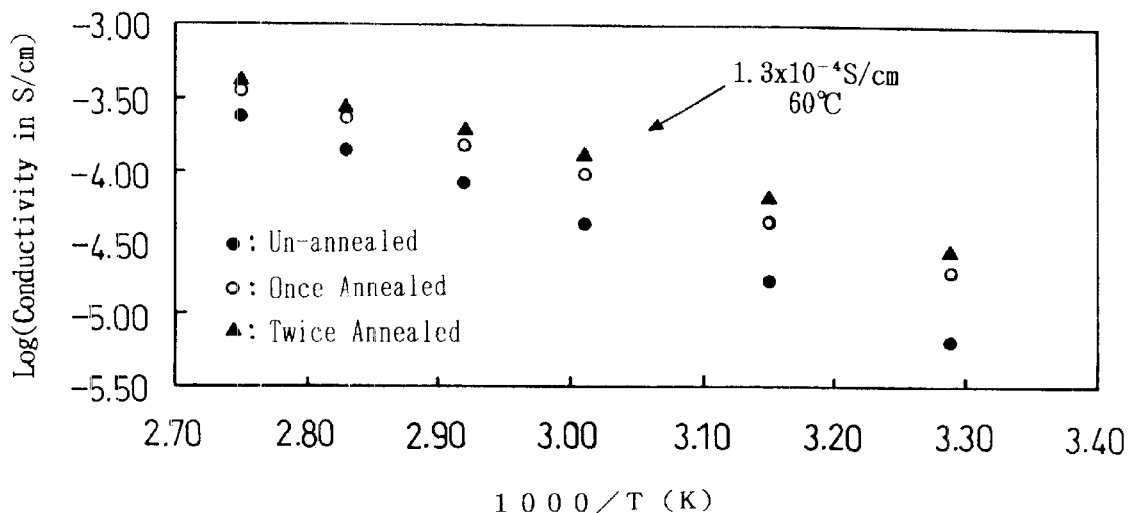
FIG. 5 is a diagram illustrating the relationship between the annealing treatment and the ionic conductivity in an ionic conductor of Example No. 11.

The ionic conductivities of the three kinds of the ionic conductors, the un-annealed sample, the annealed sample 1 and the twice-annealed sample 2 were examined in the temperature range of from room temperature to 90° C. FIG. 5 illustrates the results of the measurements. In FIG. 5, the solid circles identify the ionic conductivities of the un-annealed sample. The blank circles identify the ionic conductivities of the once annealed sample 1. The solid triangles identify the twice-annealed sample. The horizontal axis specifies the measurement temperatures, and the vertical axis specifies the ionic conductivities.

In the ionic conductors of Example No. 11, it can be seen that the ionic conductivities increased remarkably with the annealing treatment. It can also be seen that the ionic conductivities were further increased by carrying out the annealing treatment twice. It was further confirmed that there was an ionic conductor of Example No. 11 which exhibited a high ionic conductivity, $10^{-4}$ $Scm^{-1}$ at 60° C. after the annealing treatment.

EXAMPLE NO. 12

In Example No. 12, the relationship between the electrolyte salt: ionically conducting molecule ratio, ionic conductivity and the effect of the annealing treatment was investigated. Samples were prepared as follows: namely; an un-annealed sample which included the electrolyte salt in an equal molar ratio with respect to the ionically conducting molecule, and which was prepared in the same manner as Example No. 11; an annealed sample which was made by annealing the un-annealed sample twice; a second un-annealed sample which contained an electrolyte salt: ionically conducting molecule molar ratio of 1:2 (i.e., the ionically conducting molecule was included in an amount that was twice that of the electrolyte salt), and which was prepared in the same manner as Example No. 11; and a second annealed sample which was made by annealing the second un-annealed sample twice. Thus, the ionic conductivities of 4 kinds of ionic conductors in total were examined in the temperature range of from room temperature to 90° C.

Figure 6:
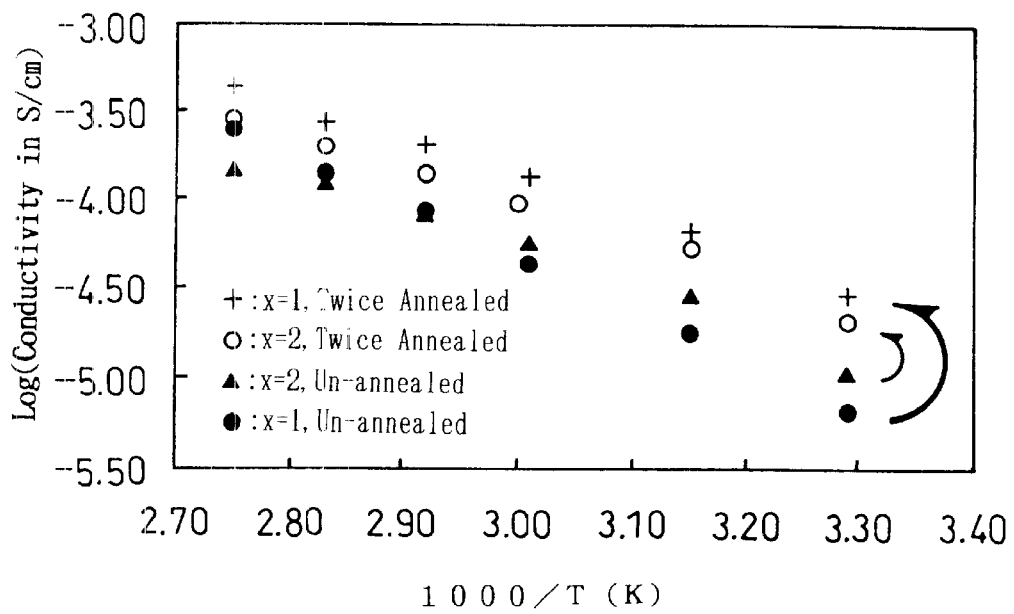
FIG. 6 is a diagram illustrating the relationship between the annealing treatment and the ionic conductivity in an ionic conductor of Example No. 12.

The results are shown in FIG. 6. In FIG. 6, the solid circles and the "+" identify the ionic conductors which contained the electrolyte salt for ionic conduction in an equal molar ratio with respect to the ionically conducting molecule; the solid triangles and the blank circles identify the ionic conductors which contained the electrolyte salt with respect to the ionically conducting molecule in a molar ratio of 1:2; the solid circles and the solid triangles identify the ionic conductors which were un-annealed; and the blank circles and "+" identify the ionic conductors which were annealed twice.

When the samples, in which the electrolyte salt: ionically conducting molecule molar ratio was 1:1 are compared with the samples in which the ratio was 2:1, the un-annealed samples exhibited low ionic conductivities. However, when the un-annealed samples were annealed twice, the ionic conductivities increased greatly and samples with a ratio of 1:1 increased more than those with a molar ratio of 2:1. The reason for this phenomenon is believed to be as follows. The boroxine compound (i.e., ionically conducting molecule) and the lithium salt underwent more efficient organization as a result of the heat treatment because they were present in an equal amounts.

EXAMPLE NO. 13

In Example No. 13, Bx(C1204) illustrated by structural formula (7) below was used instead of the ionically conducting molecule used in Example No. 11. An ionic conductor of Example No. 13 was prepared which included the ionically conducting molecule in an amount of 40% by weight and an ethylene oxide-propylene oxide copolymer, working as the structural member, in an amount of 60% by weight. In the ethylene oxide-propylene oxide, the ratio of the ethylene oxide with respect to the propylene oxide was 90:10 by mol (i.e., EO:PO=90:10 by mol). Moreover, $LiCF_3SO_3$ (LiTrif), working as the electrolyte salt for ionic conduction, was added in an equal molar amount to that of the Bx(C1204). Except the arrangements described above, the ionically conducting film was prepared in the same manner as the samples of Example No. 11.

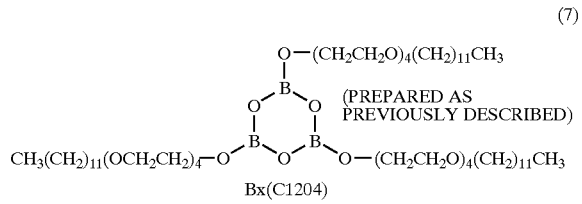

(7)

Bx(C1204) (PREPARED AS PREVIOUSLY DESCRIBED)

This ionic conductor was labeled as an un-annealed sample of Example No. 13. Further, the ionic conductor was heated at 90° C. for 2 hours, was cooled slowly to 35° C. over a period of 4 hours, and was left at room temperature for 15 hours or more. Thus, an annealed sample 1 was obtained. The annealing treatment was carried out twice. Thus, a twice-annealed sample 2 was obtained.

Figure 7:
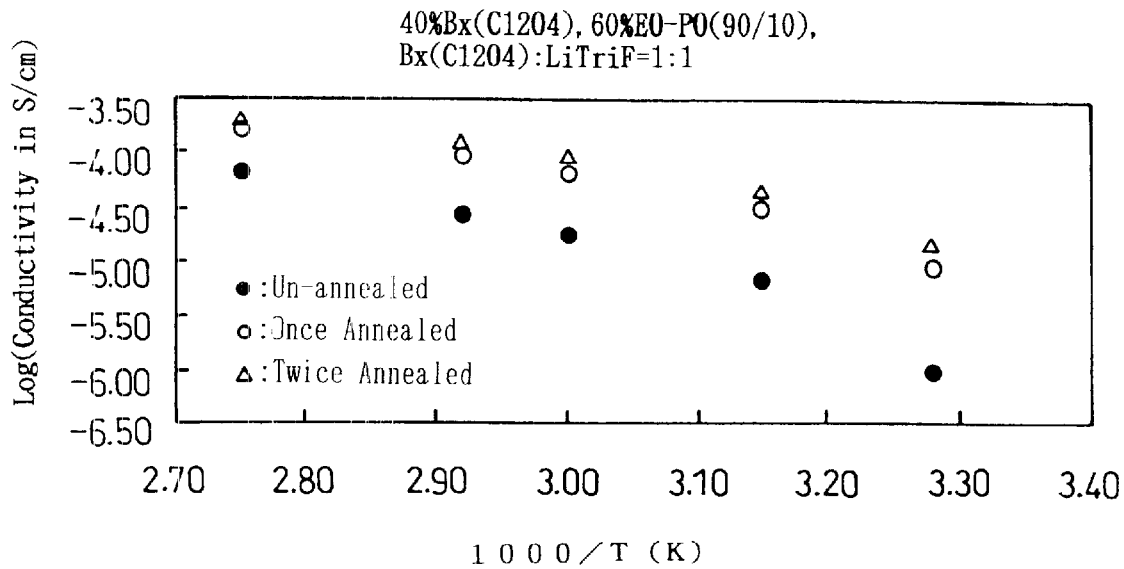
FIG. 7 is a diagram illustrating the relationship between the annealing treatment and the ionic conductivity in an ionic conductor of Example No. 13.

The ionic conductivities of the three kinds of ionic conductors, the un-annealed sample, the annealed sample 1 and the twice-annealed sample 2, were measured in the temperature range of from room temperature to 90° C. FIG. 7 illustrates the results of the measurements. In FIG. 7, the solid circles identify the ionic conductivities of the un-annealed sample. The blank circles identify the ionic conductivities of the once annealed sample 1. The blank triangles identify the twice-annealed sample 2.

In the ionic conductors of Example No. 13, it can also be seen that the annealing treatment remarkably increased the ionic conductivities. It can be also appreciated that the ionic conductivities were further increased by carrying out the annealing treatment twice.

Table 9 summarizes the advantages of the annealing treatment in Example Nos. 11, 12 and 13. The following can be understood from Table 9. The annealing treatment was most effective for ionic conductivity enhancement when the molar ratio of the ionically conducting molecule: lithium salt was 1:1: namely; when the boroxine compound and the lithium salt were included in equal molar quantities. The heating treatment was most effective for conductivity enhancement when the boroxine compound had long chain alkyl groups. It is believed that these enhancements are effected greatly by orientation of the boroxine compound, working as the ionically conducting molecule of the present invention, and that the organization of the boroxine compound and the ethylene oxide-propylene oxide, working as the structural member of the present invention, is more efficient. It should be particularly noted that the ionic conductor, which employed the Bx(3) set forth in Table 7, and in which the boroxine compound and the lithium salt were present in equal molar quantities (i.e., 1:1), and which was annealed twice, exhibited a high ionic conductivity of $1.3 \times 10^{-4}$ Scm$^{-1}$ at 60° C.

TABLE 9

| | | Ionic Conductivity (Scm$^{-1}$) | | |
|---|---|---|---|---|
| | | Bx(3) 2:1 | Bx(3) 1:1 | Bx(C1240) |
| Un-an-nealed | 30° C. | $1.0 \times 10^{-5}$ | $6.8 \times 10^{-6}$ | $9.0 \times 10^{-7}$ |
| | 60° C. | $5.6 \times 10^{-5}$ | $4.4 \times 10^{-5}$ | $1.7 \times 10^{-5}$ |
| Twice-an-nealed | 30° C. | $2.1 \times 10^{-5}$ | $2.9 \times 10^{-5}$ | $1.5 \times 10^{-5}$ |
| | 60° C. | $9.1 \times 10^{-5}$ | $\underline{1.3 \times 10^{-4}}$ | $9.0 \times 10^{-5}$ |
| | | 40% EO-PO, 60% Bx Bx:LiTrif = X:1 | 60% EO-PO, 40% Bx Bx:LiTrif = 1:1 | |

EXAMPLE NO. 14

In Example No. 14, the effects of different polymers, working as the structural member, were investigated. Instead of the ionically conducting molecule of Example No. 11, an asymmetric boroxine compound, Bx(7.2, 7.2, C18) produced in the same manner as Example No. 3, was used. Two structural members were used. For example, an ethylene oxide-polypropylene oxide (EO-PO) copolymer and poly (methyl methacrylate) (PMMA) were used as the structural member. The molar ratio of EO with respect to PO was 90/10 in the EO-PO copolymer. The ionic conductors of Example No. 14 contained 30 weight % of the ionically conducting molecule, and 70 weight % of the polymer acting as the structural member. LiCF$_3$SO$_3$ (LiTrif), the electrolyte salt for ionic conduction, was added in an equal molar quantity to that of the Bx(7.2, 7.2, C18). Except the arrangements described above, the ionic conductors were prepared as films in the same manner as those of Example No. 11.

These ionic conductors were labeled as un-annealed samples of Example No. 14. Further, the ionic conductors were heated at 90° C. for 2 hours, were cooled slowly to 35° C. over a period of 4 hours, and were left at room temperature for 15 hours or more. The annealing treatment was carried out twice. Thus, annealed samples were obtained.

Figure 8:
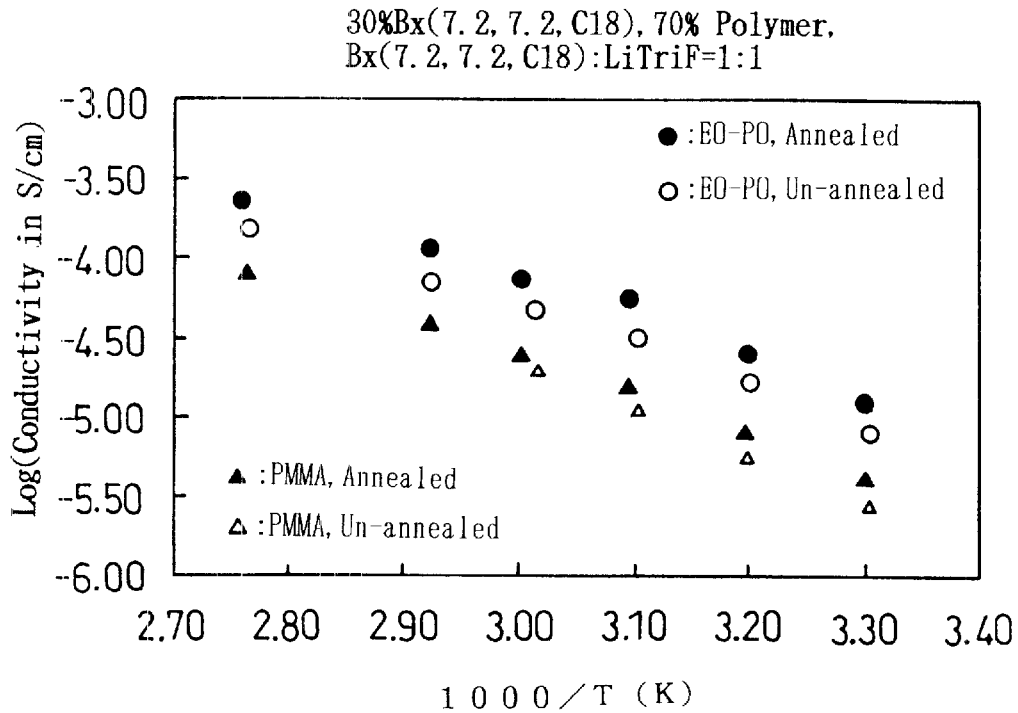
FIG. 8 is a diagram illustrating the relationship between the annealing treatment and the ionic conductivity in an ionic conductor of Example No. 14.

The ionic conductivities of four kinds of the ionic conductors in total, the un-annealed samples and the annealed samples, were measured in the temperature range of from room temperature to 90° C. FIG. 8 illustrates the results of the measurements. In FIG. 8, the blank circles identify the ionic conductivities of the un-annealed sample in which EO-PO was used as the structural member. The solid circles identify the ionic conductivities of the annealed sample in which EO-PO was used as the structural member. The blank triangles identify the ionic conductivities of the un-annealed sample in which PMMA was used as the structural member. The solid triangles identify the ionic conductivities of the annealed sample in which PMMA was used as the structural member.

In the ionic conductors in which the structural member was PMMA, the conductivity enhancement resulting from the annealing treatment were relatively small. In the low temperature region, the ionic conductivity was improved slightly. However, in the high temperature region, it was observed that the ionic conductivity negligibly increased.

In the ionic conductors in which the structural member was the EO-PO, the ionic conductivity was improved not only in the low temperature region but also in the high temperature region. These phenomena indicate that the ionic conductivity was improved less by the annealing treatment when PMMA was used as the structural member.

EXAMPLE NO. 15

In Example No. 15, the effects of plasticizer addition to the PMMA (e.g., structural member) were examined. As an ionically conducting molecule, an asymmetric boroxine compound, Bx(3, 3, C14), illustrated by the structural formula (8) below was used. 2 kinds of ionic conductors were prepared, namely; in the first case, poly(methyl methacrylate) (PMMA) free from a plasticizer; and in the second case, PMMA including 35.8 weight % polyethylene glycol dimethyl ether (average molecular weight: 250), working as a plasticizer, were prepared. The ionic conductors contained a weight ratio ionically conducting molecule: structural member of 70:30. LiCF$_3$SO$_3$ (LiTrif), the electrolyte salt for ionic conduction, was added in an equal molar quantity to that of the ionically conducting molecule Bx(3, 3, C14). The ionic conductors were prepared as films in the same manner as those of Example No. 11.

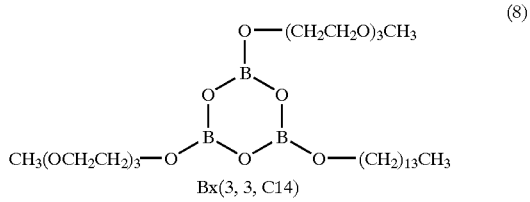

Bx(3, 3, C14)

These ionic conductors were labeled as un-annealed samples of Example No. 15. Further, the ionic conductors were heated at 90° C. for 2 hours, were cooled slowly to 35° C. over a period of 4 hours, and were left at room temperature for 15 hours or more. The annealing treatment was carried out twice. Thus, annealed samples were obtained.

Figure 9:
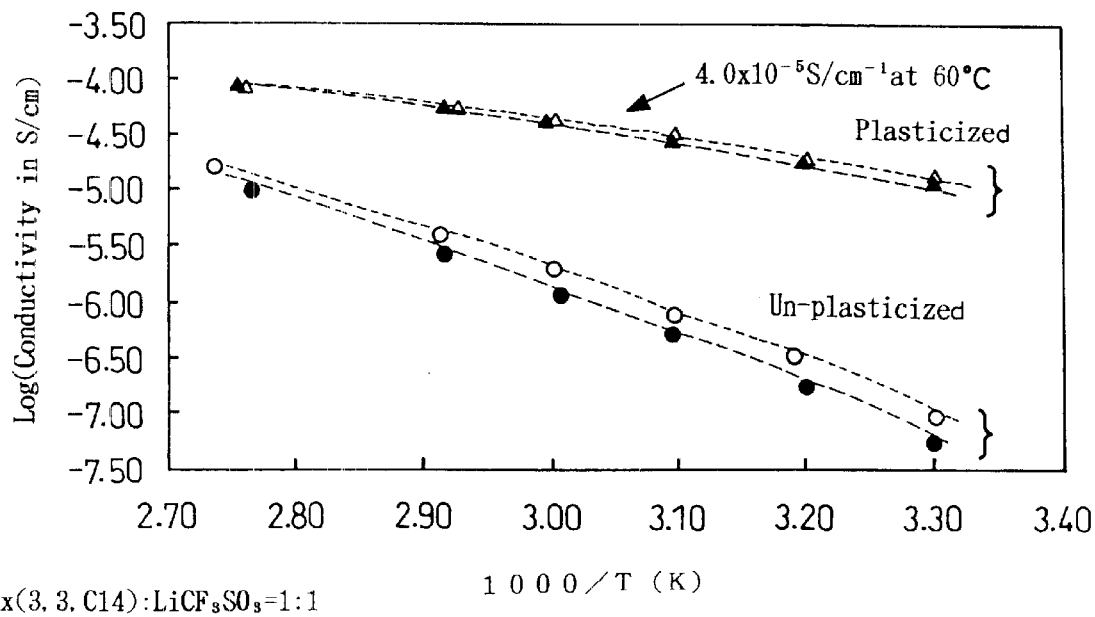
FIG. 9 is a diagram illustrating the relationship between the annealing treatment and the ionic conductivity in an ionic conductor of Example No. 15.

The ionic conductivities of four kinds of ionic conductors in total, the un-annealed samples and the annealed samples, were measured in the temperature range of from room temperature to 90° C. FIG. 9 illustrates the results of the measurements. In FIG. 9, the solid circles identify the ionic conductivities of the un-annealed sample which contained PMMA and was free from plasticizer. The blank circles identify the ionic conductivities of the annealed sample which contained PMMA and was free from plasticizer. The solid triangles identify the ionic conductivities of the un-annealed sample which contained PMMA with added plasticizer. The blank triangles identify the ionic conductivities of the annealed sample which contained PMMA with added plasticizer.

According to FIG. 9, it can be seen that conductivity enhancement resulting from the annealing treatment was not observed when plasticizer was added. However, it is seen that ionic conductivities increased sharply when plasticizer was added.

EXAMPLE NO. 16

In Example No. 16, the ionic conductivities of ionic conductors were examined when polybutyl methacrylate (PBMA) illustrated in structural formula (9) below and having a slightly longer alkyl chain was used as the structural member. The ionically conducting molecule, Bx(3, 3, C14), was used which was an asymmetric boroxine compound having a long chain alkyl chain. The ionic conductor of Example No. 16 was composed of 70 weight % of the ionically conducting molecule and 30 weight % of the structural member. Moreover, LICF$_3$SO$_3$ (LiTrif), as the electrolyte salt for ionic conduction, was added in an equal molar quantity to that of the Bx(3, 3, C14). Except the arrangements described above, the ionically conducting film was prepared in the same manner as the samples of Example No. 11.

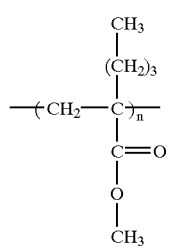

(9)

The ionic conductor was labeled as an un-annealed sample of Example No. 16. Further, the ionic conductor was heated at 90° C. for 2 hours, was cooled slowly to 35° C. over a period of 4 hours, and was left at room temperature for 15 hours or more. Thus, an annealed sample 1 ws obtained. The annealing treatment was carried out twice. Thus, a twice-annealed sample was obtained.

Figure 10:
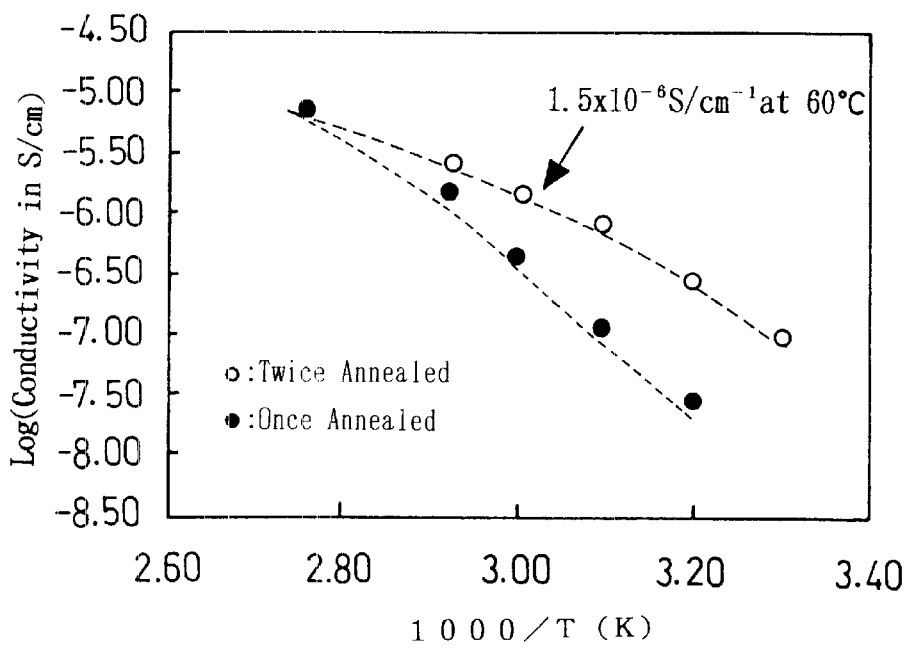
FIG. 10 is a diagram illustrating the relationship between the annealing treatment and the ionic conductivity in an ionic conductor of Example No. 16.

The ionic conductivities of three kinds of the ionic conductors, the un-annealed sample, the annealed sample 1 and the twice-annealed sample 2 were measured in the temperature range of from room temperature to 90° C. FIG. 10 illustrates the results of the measurements. In FIG. 10, the solid circles identify the ionic conductivities of the once annealed sample 1. The blank circles identify the twice-annealed sample 2. Note that, since the ionic conductivities of the un-annealed sample were extremely low, they are not illustrated in FIG. 10.

Of the ionic conductors of Example No. 16, it was observed that the un-annealed sample exhibited extremely low ionic conductivities. However, after annealing treatment, the ionic conductivities improved remarkably. It is believed that the annealing treatment resulted in the conductivity enhancement in the following manner. The PBMA, working as the structural member, the boroxine compound and the lithium salt were organized by heating, thereby enhancing the ionic conductivities.

EXAMPLE NO. 17

Figure 11:
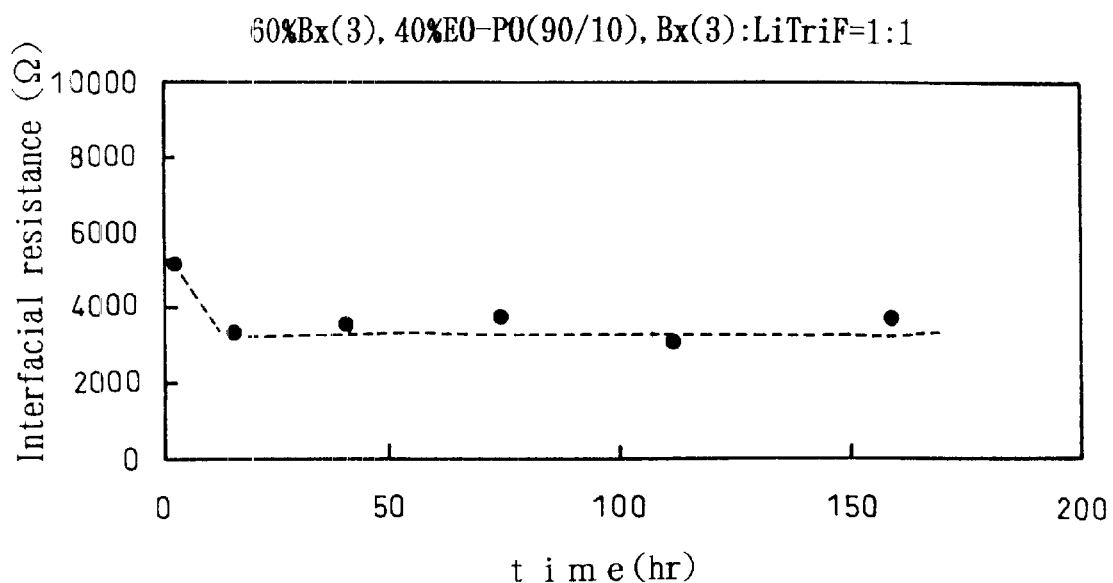
FIG. 11 is a diagram illustrating the relationship between the time and the interfacial resistance between an ionic conductor of Example No. 17 and metallic lithium.

In Example No. 17, the ionic conductor prepared in Example No. 11 was used as a polymer electrolyte film, and the time dependence of the interfacial resistance between itself and a metallic lithium electrode was measured by the AC impedance method. FIG. 11 illustrates the results of the measurement. The interfacial resistance decreased as time elapsed, and reached about 3,500Ω after approximately 20 hours. It was constant thereafter. Namely, the following were verified. The interfacial resistance became constant, and was stabilized with time. The stabilization of lithium/electrolyte interfacial resistance is a favorable property for battery materials.

On the other hand, the ionic conductor, which was made from the structural member and lithium salt, and which was free from the present ionically conducting molecule, exhibited an interfacial resistance larger than that of the present ionic conductor by 2 orders of magnitude. Moreover, the following phenomena were observed. The interfacial resistance decreased with time for the first 20 hours, but started increasing after 20 hours passed. Such an ionic conductor, which exhibits unstable interfacial resistance, is difficult to utilize as a material for batteries.

Having now fully described the present invention, it will be apparent to one of ordinary skill in the art that many changes and modifications can be made thereto without departing from the spirit or scope of the present invention as set forth herein including the appended claims.

What is claimed is:

1. An ionic conductor, comprising:
   an electrolyte salt for ionic conduction;
   an ionically conducting molecule including an ether chain which provides an ion conducting pathway and a boroxine ring bonded to the ether chain and trapping anions resulting from said electrolyte salt; and
   a structural member for dispersion and immobilization of said ionically conducting molecule and said electrolyte salt therein.

2. The ionic conductor according to claim 1, wherein the ether chain is (—CH$_2$—CH$_2$—O—).

3. The ionic conductor according to claim 1, wherein said structural member is at least one member selected from the group consisting of ethylene oxide-propylene oxide copolymer, poly(methyl methacrylate), poly(oligoethylene glycol methacrylate), polyvinyl chloride and poly(vinylidene fluoride-co-hexafluoropolypropylene).

4. The ionic conductor according to claim 1, wherein said electrolyte salt is a lithium salt.

5. A process for producing an ionic conductor, comprising the steps of:
   synthesizing an ionically conducting molecule including an ether chain which provides an ion conducting pathway and a boroxine ring bonded to the ether chain and trapping anions; and
   dispersion and immobilization of the ionically conducting molecule and an electrolyte salt for ionic conduction in a structural member by compounding the ionically conducting molecule, the electrolyte salt and the structural member.

6. The process according to claim 5 further comprising a step of annealing the resulting ionic conductor by a heat treatment after said dispersion-and-immobilization step.

* * * * *